US008148291B2

(12) United States Patent
Sudo et al.

(10) Patent No.: US 8,148,291 B2
(45) Date of Patent: Apr. 3, 2012

(54) METHOD FOR MANUFACTURING CATALYST FOR USE IN PRODUCTION OF METHACRYLIC ACID

(75) Inventors: Atsushi Sudo, Takasaki (JP); Tatsuhiko Kurakami, Sanyoonoda (JP); Toshitake Kojima, Takasaki (JP); Shigeo Hayashimoto, Tokyo (JP); Yasushi Kobayashi, Sanyoonoda (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/155,863

(22) Filed: Jun. 8, 2011

(65) Prior Publication Data

US 2011/0237829 A1    Sep. 29, 2011

Related U.S. Application Data

(62) Division of application No. 11/919,911, filed as application No. PCT/JP2006/309452 on May 11, 2006, now Pat. No. 8,017,547.

(30) Foreign Application Priority Data

May 12, 2005  (JP) .................................. 2005-140037

(51) Int. Cl.
*B01J 23/00* (2006.01)
(52) U.S. Cl. ........ 502/318; 502/200; 502/211; 562/524; 562/535
(58) Field of Classification Search .................. 502/200, 502/211; 562/524, 535; *B01J 23/00, 27/186, B01J 27/19*
See application file for complete search history.

(56) References Cited

U.S. PATENT DOCUMENTS

| | | | |
|---|---|---|---|
| 4,225,466 A | 9/1980 | Wada et al. | |
| 4,259,211 A | 3/1981 | Krabetz et al. | |
| 5,198,579 A | 3/1993 | Honda et al. | |
| 5,716,895 A | 2/1998 | Sugi et al. | |
| 7,825,061 B2 | 11/2010 | Sudo et al. | |
| 8,017,547 B2 * | 9/2011 | Sudo et al. ................... | 502/318 |
| 2002/0052529 A1 | 5/2002 | Kase et al. | |
| 2007/0010394 A1 * | 1/2007 | Atsushi et al. ............... | 502/200 |
| 2009/0234158 A1 | 9/2009 | Sudo et al. | |

FOREIGN PATENT DOCUMENTS

| | | | |
|---|---|---|---|
| DE | 19922156 | * | 8/2000 |
| EP | 1325780 A1 | | 7/2003 |
| EP | 1595600 A1 | | 11/2005 |
| JP | 57-165040 A | | 10/1982 |
| JP | 4-63139 A | | 2/1992 |
| JP | 8-157414 A | | 6/1996 |
| JP | 9-75740 A | | 3/1997 |
| JP | 9-290162 A | | 11/1997 |
| JP | 9-299803 A | | 11/1997 |
| JP | 2003-10691 A | | 1/2003 |
| JP | 2004-188231 A | | 7/2004 |
| JP | 2005-21727 A | | 1/2005 |
| JP | 2005-58909 A | | 3/2005 |
| JP | 2005-131577 A | | 5/2005 |
| JP | 2005-187463 A | | 7/2005 |
| JP | 2005-272313 A | | 10/2005 |
| WO | 2004/73857 A1 | | 9/2004 |

OTHER PUBLICATIONS

Machine translation of DE19922156 detailed description.*
English translation of Cox (DE19922156).*
International Search Report dated Jul. 4, 2006 in corresponding foreign application No. PCT/JP2006/309452.
Singapore Communication dated May 27, 2009 in corresponding foreign patent application No. SG 200717441-0.
Chinese Communication, with English translation, dated Jun. 23, 2009 in corresponding foreign patent application No. CN 2006800163159.
Chinese Communication, with English translation, dated Feb. 5, 2010 in corresponding foreign patent application No. CN 2006800163159.
Chinese Communication, with English translation, dated Aug. 4, 2010 in corresponding foreign patent application No. CN 2006800163159.
Indonesian Communication dated Feb. 17, 2011 in corresponding foreign patent application No. W-00 2007 03746.
International Search Report dated Apr. 25, 2006 in co-pending foreign patent application No. PCT/JP2006/306318.
European Communication dated Jul. 31, 2009 in co-pending foreign patent application No. EP 06730266.1.
Chinese Communication, with English Translation, dated Sep. 25, 2009 in co-pending foreign patent application No. CN 2006800093175.
Singapore Communication dated Dec. 3, 2009 in co-pending foreign patent application No. SG 200708866-9.
European Communication dated May 28, 2010 in co-pending foreign patent application No. EP 06730266.1.
European Communication dated May 28, 2010 in co-pending foreign patent application No. EP 10156028.2.
Singapore Communication dated Nov. 9, 2010 in co-pending foreign patent application No. SG 200708866-9.
Chinese Communication, with english translation, dated Jan. 26, 2011 in co-pending foreign patent application No. CN 201010143947X.
Office Action dated Jul. 1, 2010 in co-pending U.S. Appl. No. 11/887,017.

(Continued)

*Primary Examiner* — Melvin Mayes
*Assistant Examiner* — Jun Li
(74) *Attorney, Agent, or Firm* — Nields, Lemack & Frame, LLC

(57) ABSTRACT

It is an object of the present invention to provide a catalyst having excellent performance and high mechanical strength for use in the production of methacrylic acid. A method for manufacturing a catalyst comprising essential active components of molybdenum, phosphorus, vanadium, cesium, ammonia, copper, and antimony for use in the production of methacrylic acid, comprising drying a slurry prepared by mixing a compound(s) containing the essential active components with water and then calcining the resulting dry powder and molding the calcined powder.

4 Claims, No Drawings

OTHER PUBLICATIONS

Final Rejection dated Mar. 15, 2011 in co-pending U.S. Appl. No. 11/887,017.
Office Action dated Feb. 25, 2011 in corresponding U.S. Appl. No. 11/919,911.
Notice of Allowance dated Jun. 9, 2011 in corresponding U.S. Appl. No. 11/919,911.
European Communication dated Oct. 7, 2011 in co-pending European Patent Application No. EP 06730266.1.

* cited by examiner

METHOD FOR MANUFACTURING CATALYST FOR USE IN PRODUCTION OF METHACRYLIC ACID

This application is a Divisional of U.S. patent application Ser. No. 11/919,911 filed Jan. 18, 2008, which is a 371 of PCT/JP2006/309452 filed May 11, 2006, which claims priority of Japanese Patent Application No. 2005-140037 filed May 12, 2005, the disclosures of which are incorporated herein by reference.

FIELD OF THE INVENTION

The present invention relates to a method for manufacturing a catalyst for use in the production of methacrylic acid including gas-phase catalytic oxidation of methacrolein, isobutyraldehyde, or isobutyric acid using a highly active and highly selective heteropolyacid catalyst having a sufficient mechanical strength.

BACKGROUND ART

Many catalysts have been proposed for use in the production of methacrylic acid by the gas-phase catalytic oxidation of methacrolein, isobutyraldehyde, or isobutyric acid. Most of these catalysts contain molybdenum and phosphorus as the main components and have a structure of heteropolyacid and/or salt thereof. A heteropolyacid catalyst has problems of poor moldability and low mechanical strength after molding.

Much less propositions have been made to improve the mechanical strength of a heteropolyacid catalyst than propositions to improve the performance of the catalyst, for example, the yield of methacrylic acid. Patent Document 1 proposes a molding method in which heat-resistant fiber, such as ceramic fiber, is mixed as a reinforcing agent.

Patent Document 2 proposes a molding method of a catalyst containing essential components of molybdenum and phosphorus, in which its oxide precursor and an oxide are mixed and molded.

[Patent Document 1] Japanese Patent Publication No. 2-36296
[Patent Document 2] Japanese Patent Application Laying-open No. 2004-351297

SUMMARY OF THE INVENTION

However, according to findings of the present inventors, even these proposed means provide insufficient mechanical strength for an industrial catalyst, exhibit low production yields because of poor moldability, and have increased manufacturing costs. Furthermore, low mechanical strength may result in detachment of an active component while a catalyst is charged into a reaction tube. Thus, required performance cannot be achieved. Hence, further improvement is desired.

Currently proposed catalysts for use in the production of methacrylic acid are lower in both reactivity and the selectivity to a target substance and are also shorter in life than molybdenum-vanadium catalysts proposed for the production of acrylic acid by an oxidation reaction of acrolein, which is known to be similar to the gas-phase catalytic oxidation reaction of methacrolein, isobutyraldehyde, or isobutyric acid. Thus, although some of the proposed catalysts are commercialized, there is a demand for improved performance of these catalysts.

In a partly neutralized heteropolyacid salt containing essential components of molybdenum, phosphorus, vanadium, cesium, ammonia, copper, and antimony, through an intensive study to increase the mechanical strength and the yield of methacrylic acid, the present inventors found that calcination of granules, obtained by drying its precursor slurry or aqueous solution, before molding remarkably improves the moldability, to produce a catalyst having industrially satisfying mechanical strength. The present invention is thus accomplished. Thus, the present invention relates to:

(1) a catalyst comprising essential active components of molybdenum, phosphorus, vanadium, cesium, ammonia, copper, and antimony for use in the production of methacrylic acid and a method for manufacturing the catalyst, comprising drying a slurry prepared by mixing a compound(s) containing the essential active components with water and then calcining the resulting dry powder and molding the calcined powder;

(2) a method for manufacturing a catalyst comprising essential active components of molybdenum, phosphorus, vanadium, cesium, ammonia, copper, and antimony for use in the production of methacrylic acid, comprising drying a slurry prepared by mixing a compound(s) containing the essential active components other than antimony with water and then calcining a mixture of the resulting dry powder and a compound containing antimony and molding the calcined mixture;

(3) a method for manufacturing a catalyst comprising essential active components of molybdenum, phosphorus, vanadium, cesium, ammonia, copper, and antimony for use in the production of methacrylic acid, comprising drying a slurry prepared by mixing a compound(s) containing the essential active components other than antimony with water, calcining the resulting dry powder, and molding a mixture of the calcined powder and a compound containing antimony;

(4) the method for manufacturing a catalyst according to any one of (1) to (3), wherein the calcination temperature is 200° C. to 450° C.;

(5) the method for manufacturing a catalyst according to any one of (1) to (4), wherein the molding of a powder after the calcination comprises coating an inert carrier with the powder using a binder to form a coated catalyst;

(6) the method for manufacturing a catalyst according to (5), wherein the binder is water and/or at least one type of liquid selected from the group consisting of an organic compound having a boiling point of 150° C. or less at 1 atmospheric pressure;

(7) the method for manufacturing a catalyst according to any one of (1) to (6), wherein a molded product after the molding is calcined at 100° C. to 450° C.; and (8) a method for producing methacrylic acid, comprising gas-phase catalytic oxidation of methacrolein, isobutyraldehyde, or isobutyric acid using a catalyst according to any one of (1) to (8).

ADVANTAGES EFFECT OF THE INVENTION

According to the present invention, a highly active and highly selective catalyst containing essential components of molybdenum, phosphorus, vanadium, cesium, ammonia, copper, and antimony and having high mechanical strength can be manufactured.

DESCRIPTION OF THE PREFERRED EMBODIMENTS

A manufacturing method according to the present invention includes preparing an aqueous solution containing a compound(s) containing active components (molybdenum, phosphorus, vanadium, cesium, ammonia, copper, and antimony; hereinafter referred to as essential components) of a catalyst or an aqueous dispersion of the compound(s) (hereinafter collectively referred to as slurry), calcining a dry powder prepared by drying the aqueous solution or the aqueous dispersion (this step is hereinafter referred to as precalcination), and molding the precalcined powder. A calcination step (main calcination) may follow the molding step.

Furthermore, in the present invention, a compound(s) containing the active components in the preparation of the slurry does not necessarily contain all the active components. Part of the components may be added after the precalcination.

In the present invention, a metallic element other than essential components may be included as an active component. Examples of a metallic element other than essential components include at least one element selected from the group consisting of arsenic, silver, manganese, zinc, aluminum, boron, germanium, tin, lead, titanium, zirconium, chromium, rhenium, bismuth, tungsten, iron, cobalt, nickel, cerium, thorium, potassium, and rubidium. A metallic element other than the essential components may be added in any manner, provided that local concentration distribution of the components does not occur, and may be added (a) during the preparation of slurry, (b) before precalcination, and (c) after a precalcination step and before a molding step. (b) or (c) is preferred.

In the present invention, the atomic ratio of a compound containing an active component to 10 molybdenum atoms is generally 0.1 to 6, preferably 0.3 to 2.0 for vanadium, generally 0.5 to 6, preferably 0.7 to 2.0 for phosphorus, generally 0.01 to 4.0, preferably 0.1 to 2.0 for cesium, generally 0.1 to 10.0, preferably 0.5 to 5.0 for ammonia (typically contained as an ammonium group), and generally 0.01 to 5, preferably 0.05 to 2.0 for antimony. The type and the amount of another optional active component are determined as appropriate to provide a catalyst having optimum performance depending on the condition under which the catalyst is used. The atomic ratio (composition) of a catalyst described in the present invention is that in the preparation of raw materials and does not contain oxygen.

An embodiment will be described below for the steps described above.

Preparation of Slurry

In the present invention, examples of a compound containing an active component for use in the preparation of a catalyst include a chloride, a sulfate, a nitrate, an oxide, or an acetate of an active component element. Specifically, preferred examples of a compound containing an active component include a nitrate, such as potassium nitrate or cobalt nitrate, an oxide, such as molybdenum oxide, vanadium pentoxide, antimony trioxide, cerium oxide, zinc oxide, or germanium oxide, and an acid (or salt thereof), such as orthophosphoric acid, phosphoric acid, boric acid, aluminum phosphate, or 12 tungstophosphoric acid. Preferably, a cesium compound is cesium acetate or cesium hydroxide and a weak acid salt of cesium. Preferably, an ammonium compound is ammonium acetate or ammonium hydroxide. Preferred examples of a copper compound include copper acetate (cuprous acetate, cupric acetate, basic copper acetate, or cupric oxide, preferably cupric acetate) or copper oxide (cuprous oxide, cupric oxide). Each of the compounds containing an active component may be used singly or in combination. A slurry can be formed by uniformly mixing each compound containing an active component and water. Preferably, in the preparation of the slurry, a compound containing molybdenum, vanadium, phosphorus, and another optional metallic element is sufficiently dissolved before the addition of a compound containing cesium, a compound containing ammonium, and a compound containing a copper to the slurry. Preferably, when a compound containing antimony is added in the preparation of slurry, it is added lastly after the other compounds containing the essential active components are added. More preferably, after a slurry containing active components other than a compound containing antimony is prepared and is dried, the dried powder and the compound containing antimony are mixed and calcined, or the dried powder is calcined and is then mixed with the compound containing antimony. In the preparation of a slurry, the slurry is preferably heated to a temperature at which a compound containing molybdenum, phosphorus, vanadium, and another optional metallic element can be dissolved sufficiently. The temperature at which a compound containing cesium and a compound containing ammonium are added is generally 0° C. to 35° C., preferably about 10° C. to about 30° C. This tends to provide a catalyst having a higher activity. Thus, the temperature is preferably decreased to 10° C. to 30° C. The amount of water in the slurry is not limited, provided that the whole quantity of compounds used in the slurry can completely be dissolved or uniformly be mixed, and is determined as appropriate in consideration of a drying method or drying conditions. In general, the amount of water in the slurry is about 200 to 2000 parts by weight per 100 parts by weight of the total compounds used in the preparation of the slurry. While a larger amount of water maybe used, an excessive amount of water causes many demerits, such as an increase in the energy cost of a drying step and insufficient drying of the slurry.

Drying

Then, the slurry formed in the step described above is dried into a dry powder. The slurry may be dried by any method, provided that the slurry is completely dried. Examples of a drying method include drum drying, freeze-drying, spray drying, and evaporation to dryness. Among them, the spray drying is particularly preferred in the present invention, because it can dry the slurry into a powder or granules in a short time.

The temperature of the spray drying depends on the slurry concentration and the feed rate and is generally 70° C. to 150° C. at the outlet of a dryer. Preferably, a dry product has an average particle diameter of 30 to 700 µm.

Precalcination

Precalcination of the resulting dry powder remarkably improves the moldability and the shape and the mechanical strength of a molded catalyst. The precalcination atmosphere may be in an air current or in a current of an inert gas, such as nitrogen. An air current is industrially preferred. The precalcination temperature is 200° C. to 400° C., preferably 250° C. to 380° C., and more preferably 290° C. to 310° C. Precalcination at a temperature less than 200° C. tends to have a smaller effect on the moldability. Precalcination at a temperature more than 400° C. has an adverse effect on the catalyst performance. The precalcination time is preferably 3 to 12 hours and more preferably 5 to 10 hours. While the precalcination time may be 12 hours or more, the effect consistent with the precalcination time can hardly be achieved.

The reason for the improved moldability by precalcination is not clear. In general, a partly neutralized heteropolyacid salt, such as the catalyst described above, mostly has a so-called Dawson structure when slurry is just dried and the Dawson structure is converted into a Keggin structure by heating. The present inventors assumed that this conversion results in the improved moldability.

Molding

Then, the resulting precalcined granules are molded as described below. Molding after a molding aid, such as silica gel, diatomaceous earth, or an alumina powder is mixed with the precalcined granules is preferred because of good workability. A molding aid is generally used in an amount of 1 to 30 parts by weight per 100 parts by weight of precalcined granules. Furthermore, use of inorganic fiber, such as ceramic fiber or whiskers, inert to catalyst components as a reinforcing material as necessary is useful in increasing the mechanical strength of a catalyst. However, fibers that react with a catalyst component, such as potassium titanate whiskers or basic magnesium carbonate whiskers, are not preferred. These fibers are generally used in an amount of 1 to 30 parts by weight per 100 parts by weight of precalcined granules.

To reduce pressure loss of a reactant gas, precalcined granules prepared as described above or a mixture of the precalcined granules, a molding aid, and a reinforcing material are used after they are molded in a columnar, tablet, ring, spherical, or another shape. Among these, coating inert carriers with precalcined granules or the mixture to provide coated catalysts is particularly preferred, because improvement in selectivity and removal of reaction heat are expected to be achieved.

Preferable coating step is a tumbling granulation method as described below. This is a method to coat carriers with precalcined granules or the mixture by, for example, rapidly rotating a flat or uneven disc in an apparatus having the disc at the inner bottom of a fixed container so as to stir carriers in the container vigorously through their repetitive rotatory motion and orbital motion and by adding binders and precalcined granules or the mixture. Any of the following methods can be employed to add binders: 1) to premix the binders in precalcined granules or a mixture, 2) to add the binders at the same time when precalcined granules or a mixture is added into the fixed container, 3) to add the binders after precalcined granules or a mixture is added into the fixed container, 4) to add the binders before precalcined granules or a mixture is added into the fixed container, and 5) to divide precalcined granules or a mixture and binders into separate pieces and add the whole amount by combining the above 2-4) as appropriate. In the case of 5), it is preferable to control addition rate using auto feeders and the like to ensure that a defined amount is carried on the carriers without, for example, adhesion of the precalcined granules or the mixture to the wall of the fixed container and aggregation between the precalcined granules or the mixture.

Binders have no limitation so long as it is water and/or at least one type of liquid selected from a group consisting of organic compounds having boiling point no more than 150° C. at one atm. By consideration of drying and the like after the coating, organic compounds having boiling point no more than 150° C. are preferred. A specific example of the binders other than water includes alcohols, preferably alcohols having 1-4 carbons, such as methanol, ethanol, propanols, butanols, ethers such as ethyl ether, butyl ether or dioxane, esters such as ethyl acetate or butyl acetate, ketones such as acetone or methyl ethyl ketone, and aqueous solutions thereof, with ethanol being particularly preferred. When ethanol is used as a binder, it is preferable to make the ethanol/water ratio being 10/0-0/10 (mass ratio), preferably 10/0-1/9 (mass ratio). The amount of these binders used is usually 10-60 parts by weight, preferably 15-40 parts by weight to 100 parts by weight of dry powder.

A specific example of carriers that can be used in the present invention includes spherical carriers etc. of silicon carbide, alumina, silica-alumina, mullite and alundum and the like, which have a diameter of 1-15 mm, preferably 2.5-10 mm. These carriers usually have a pore ratio of 10-70%. The ratio between the carriers and precalcined granules or a mixture used is usually precalcined granules or a mixture/(precalcined granules or a mixture+carriers)=10-75% by weight, preferably 15-60% by weight.

Precalcined granules or a mixture are applied to the carriers in this way, and the resulting coated products are usually approximately 3-15 mm in diameter.

Main Calcination

While coated catalysts obtained as described above may be used for gas-phase catalytic oxidation reactions as catalysts without further modification, calcination may sometimes preferably increase catalytic activity. In this case, the calcination temperature is usually 100-450° C., preferably 270-420° C. and the calcination time is 1-20 hours.

Calcination is usually conducted under air atmosphere, but it may be conducted under inert gas atmosphere such as nitrogen atmosphere. Calcination under inert gas atmosphere or reducing gas atmosphere may optionally be followed by calcination under air atmosphere.

Catalysts obtained as described above (hereinafter referred to as catalysts according to the present invention) will be used to produce methacrylic acid by gas-phase catalytic oxidation of methacrolein, isobutyraldehyde or isobutyric acid.

In the following description, a gas-phase catalytic oxidation reaction will be illustrated in which methacrolein, the most preferable raw material for use with the catalysts of the present invention, is used.

Molecular oxygen or molecular oxygen-containing gas is used in the gas-phase catalytic oxidation reaction. The ratio of molecular oxygen to methacrolein is preferably in the range of 0.5-20 molar ratio, and particularly preferably in the range of 1-10 molar ratio. It is preferable to add water into raw material gas in a molar ratio of 1-20 to methacrolein in order to promote the reaction smoothly.

In addition to oxygen and optionally water (usually included as water vapor), the raw material gas may contain gases inert to the reaction such as nitrogen, carbon dioxide and saturated hydrocarbon.

Alternatively, methacrolein may be supplied as a gas obtained from oxidation of isobutylene, tert-butanol and methyl tert-butyl ether.

The reaction temperature of a gas-phase catalytic oxidation reaction is usually 200-400° C., preferably 250-360° C. and the amount supplied of the raw material gas expressed in space velocity (SV) is usually 100-6000 hr$^{-1}$, preferably 300-3000 hr$^{-1}$.

The catalytic oxidation reaction can be conducted under either increased pressure or reduced pressure, however, pressure around atmospheric pressure is generally suitable.

EXAMPLE

The present invention will now be described more specifically by way of the examples, however, the invention is not limited to the examples.

Conversion rate, selectivity and yield are defined as follows.

Conversion rate=mole number of methacrolein reacted/mole number of methacrolein supplied×100

Selectivity=mole number of methacrylic acid produced/mole number of methacrolein reacted×100

Yield=mole number of methacrylic acid produced/mole number of methacrolein supplied×100

Example 1

1) Preparation of Catalyst

To 5680 ml of pure water were added 800 g of molybdenum trioxide, 40.43 g of vanadium pentoxide, and 73.67 g of 85% by weight orthophosphoric acid, stirred for three hours at 92° C. to yield rust-colored clear solution. The solution was then cooled to 15-20° C. and 307.9 g of an aqueous solution containing 9.1% by weight of cesium hydroxide and 689.0 g of an aqueous solution containing 14.3% by weight of ammonium acetate were gradually added with stirring, and maturation for one hour at 15-20° C. provided yellow slurry.

To the slurry, 709.9 g of an aqueous solution containing 6.3% by weight cupric acetate was gradually added, and additional maturation was performed for 30 minutes at 15-20° C.

The slurry was then spray dried to provide granules. The composition of the resulting granules was $$Mo_{10}V_{0.8}P_{1.15}Cu_{0.4}Cs_{0.3}(NH_4)_{2.3}.$$

In an air current 320 g of the granules were calcined at 310° C. for five hours to yield precalcined granules. Precalcination decreased the mass of the granules by about 4% by weight. The granules, 22.7 g of antimony trioxide, and 45 g of reinforcing material (ceramic fiber) were uniformly mixed and were applied to 300 g of spherical porous alumina carriers (particle diameter 3.5 mm) using 20% by weight ethanol aqueous solution as a binder by a tumbling granulation method, yielding a molded coated product. The resulting molded product was calcined for five hours at 380° C. in an air current to provide a desired coated catalyst.

The composition of the resulting catalyst was $$Mo_{10}V_{0.8}P_{1.15}Cu_{0.4}Cs_{0.3}(NH_4)_{2.3}Sb_{1.0}.$$

2) Catalytic Oxidation Reaction of Methacrolein 10.3 mL of the resulting coated catalyst was filled in a stainless steel reaction tube having an inner diameter of 18.4 mm. Oxidation reaction of methacrolein was performed at a raw material gas composition (mole ratio) of methacrolein:oxygen:water vapor:nitrogen=1:2:4:18.6), a space velocity (SV) of 1200 hr$^{-1}$, and a reaction bath temperature of 310° C. The reaction was performed initially at a reaction bath temperature of 310° C. for three hours and then at a reaction bath temperature of 350° C. for 15 hours (this treatment is hereinafter referred to as "high-temperature reaction treatment"). The reaction result was determined after the reaction bath temperature was decreased to 310° C.

Table 1 shows the results.

Measurement of Strength 50 g of the resulting coated catalyst was charged into a cylindrical rotating machine having a radius of 14 cm and having a baffle therein. The machine was rotated at 23 rpm for 10 minutes. After detached powder was sieved out, the remainder was measured to be 49.82 g. Thus, the percentage of the detached powder was 0.36% to the whole. This value is hereinafter referred to as friability and is listed in Table 1 together with the shape of a catalyst.

Example 2

A catalyst was prepared in the same manner as in Example 1 except that the precalcination temperature was 290° C. Oxidation reaction of methacrolein was performed and the strength was measured. Table 1 shows the results.

Example 3

A catalyst was prepared in the same manner as in Example 1 except that the precalcination temperature was 270° C. Oxidation reaction of methacrolein was performed and the strength was measured. Table 1 shows the results.

Example 4

A catalyst was prepared in the same manner as in Example 1 except that the precalcination temperature was 250° C. Oxidation reaction of methacrolein was performed and the strength was measured. Table 1 shows the results.

Example 5

A catalyst was prepared in the same manner as in Example 1 except that the precalcination temperature was 380° C. Oxidation reaction of methacrolein was performed and the strength was measured. Table 1 shows the results.

Example 6

A catalyst was prepared in the same manner as in Example 2 except that 320 g of granules after the drying step and 22.7 g of antimony trioxide were mixed before precalcination. Oxidation reaction of methacrolein was performed and the strength was measured. Table 1 shows the results.

Example 7

A catalyst was prepared in the same manner as in Example 2 except that 10 g of reinforcing material (ceramic fiber) and 335 g of spherical porous alumina carriers (particle diameter 3.5 mm) were added during coating and molding. Oxidation reaction of methacrolein was performed and the strength was measured. Table 1 shows the results.

Comparative Example 1

A catalyst was prepared in the same manner as in Example 1 except that precalcination was not performed. Oxidation reaction of methacrolein was performed and the strength was measured. Table 1 shows the results.

Comparative Example 2

To 7100 ml of pure water were added 1000 g of molybdenum trioxide and 75.81 g of vanadium pentoxide, 88.08 g of 85% by weight orthophosphoric acid, and 11.05 g of copper oxide. The mixture was heated at 92° C. for three hours with stirring to form a slurry.

The slurry was then spray dried to provide granules. The composition of the resulting granules was $$Mo_{10}V_{1.2}P_{1.1}Cu_{0.2}.$$

320 g of the granules were calcined at 290° C. for five hours in an air current to produce precalcined granules. The precalcined granules and 45 g of reinforcing material (ceramic fiber) were uniformly mixed and were applied to 300 g of spherical porous alumina carriers (particle diameter 3.5 mm) using 90% by weight ethanol aqueous solution as a binder, yielding a molded coated product. The resulting molded product was calcined for five hours at 310° C. in an air current to provide a desired coated catalyst.

As in Example 1, oxidation reaction of methacrolein was performed and the strength was measured. Table 1 shows the results.

Comparative Example 3

Oxidation reaction of methacrolein was performed and the strength was measured, as in Comparative Example 2 except that precalcination was not performed. Table 1 shows the results.

TABLE 1

Results of oxidation reaction of methacrolein and measurements of strength

| | | methacrolein conversion rate % | methacrylic acid selectivity % | methacrylic acid yield % | friability % | shape |
|---|---|---|---|---|---|---|
| Example 1 | early phase of the reaction | 82.44 | 79.97 | 65.93 | 0.36 | smooth spherical |
| | after high-temperature reaction treatment | 88.25 | 82.32 | 72.65 | | |

TABLE 1-continued

Results of oxidation reaction of methacrolein and measurements of strength

| | | methacrolein conversion rate % | methacrylic acid selectivity % | methacrylic acid yield % | friability % | shape |
|---|---|---|---|---|---|---|
| Example 2 | early phase of the reaction | 81.71 | 81.16 | 66.32 | 0.10 | smooth spherical |
| | after high-temperature reaction treatment | 87.82 | 83.61 | 73.42 | | |
| Example 3 | early phase of the reaction | 82.67 | 81.71 | 67.55 | 0.37 | slightly uneven |
| | after high-temperature reaction treatment | 88.66 | 84.37 | 74.72 | | |
| Example 4 | early phase of the reaction | 82.74 | 80.79 | 66.84 | 0.88 | slightly uneven |
| | after high-temperature reaction treatment | 87.84 | 83.60 | 73.44 | | |
| Example 5 | early phase of the reaction | 71.89 | 77.86 | 55.97 | 0.35 | smooth spherical |
| | after high-temperature reaction treatment | 79.03 | 83.24 | 65.78 | | |
| Example 6 | early phase of the reaction | 82.66 | 81.61 | 67.46 | 0.15 | smooth spherical |
| | after high-temperature reaction treatment | 87.57 | 83.28 | 72.92 | | |
| Example 7 | early phase of the reaction | 92.05 | 81.56 | 75.08 | 0.71 | smooth spherical |
| | after high-temperature reaction treatment | 91.64 | 84.14 | 77.11 | | |
| Comparative Example 1 | early phase of the reaction | 86.86 | 81.88 | 71.13 | 2.34 | uneven |
| | after high-temperature reaction treatment | 90.20 | 83.58 | 75.38 | | |
| Comparative Example 2 | early phase of the reaction | 55.43 | 81.79 | 45.34 | 0.58 | smooth spherical |
| | after high-temperature reaction treatment | 54.54 | 83.62 | 45.60 | | |
| Comparative Example 3 | early phase of the reaction | 63.50 | 79.17 | 50.28 | 1.59 | smooth spherical |
| | after high-temperature reaction treatment | 74.96 | 80.62 | 60.43 | | |

Examples 1-6 and Comparative Example 1 show that precalcination improves moldability and friability.

Example 2 and Example 6 show that the addition of antimony trioxide before precalcination has the same effect as the addition of antimony trioxide after precalcination, both providing almost the same catalyst performance.

Comparative Examples 2 and 3 show that a catalyst that does not contain some of the essential components of the catalyst according to the present invention as an active component has improved friability by precalcination, but may have much poorer performance.

Example 8

To 5680 ml of pure water were added 800 g of molybdenum trioxide, 40.43 g of vanadium pentoxide, and 73.67 g of 85% by weight orthophosphoric acid, stirred for three hours at 92° C. to yield rust-colored clear solution. The solution was then cooled to 15-20° C. and 307.9 g of an aqueous solution containing 9.1% by weight of cesium hydroxide and 689.0 g of an aqueous solution containing 14.3% by weight of ammonium acetate were gradually added with stirring, and maturation for one hour at 15-20° C. provided yellow slurry.

To the slurry, 709.9 g of an aqueous solution containing 6.3% by weight cupric acetate was gradually added, and additional maturation was performed for 30 minutes at 15-20° C. To the slurry was added 32.4 g of antimony trioxide, and maturation was performed for 30 minutes at 15-20° C.

The slurry was then spray dried to provide granules. The composition of the resulting granules was

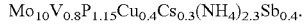

$Mo_{10}V_{0.8}P_{1.15}Cu_{0.4}Cs_{0.3}(NH_4)_{2.3}Sb_{0.4}$.

In an air current 320 g of the granules were calcined at 290° C. for five hours to yield precalcined granules. Precalcination decreased the mass of the granules by about 4% by weight. The precalcined granules and 45 g of reinforcing material (ceramic fiber) were uniformly mixed and were applied to 300 g of spherical porous alumina carriers (particle diameter 3.5 mm) using 20% by weight ethanol aqueous solution as a binder by a tumbling granulation method, yielding a molded coated product. The resulting molded product was calcined for five hours at 380° C. in an air current to provide a desired coated catalyst.

As in Example 1, oxidation reaction of methacrolein was performed and the strength was measured. Table 2 shows the results.

TABLE 2

| | | methacrolein conversion rate % | methacrylic acid selectivity % | methacrylic acid yield % | friability % | shape |
|---|---|---|---|---|---|---|
| Example 8 | early phase of the reaction | 91.61 | 78.01 | 71.46 | 0.36 | smooth spherical |
| | after high-temperature reaction treatment | 92.45 | 80.93 | 74.82 | | |

The invention claimed is:

1. A method for manufacturing a catalyst comprising essential active components of molybdenum, phosphorus, vanadium, cesium, ammonia, copper, and antimony for use in the production of methacrylic acid, comprising drying a slurry prepared by mixing a compound(s) containing the essential active components other than antimony with water to form a dry powder, calcining the resulting dry powder, and molding a mixture of the calcined powder and a compound containing antimony, wherein the molding of the mixture of the calcined powder and a compound containing antimony comprises coating an inert carrier with the mixture using a binder to form a coated catalyst.

2. The method for manufacturing a catalyst according to claim 1, wherein the calcination temperature is 200° C. to 400° C.

3. The method for manufacturing a catalyst according to claim 1, wherein the binder is water and/or at least one type of liquid selected from the group consisting of an organic compound having a boiling point of 150° C. or less at 1 atmospheric pressure.

4. The method for manufacturing a catalyst according to claim 1, wherein a molded product after the molding is calcined at 100° C. to 450° C.

* * * * *